(12) United States Patent
Soden

(10) Patent No.: US 9,272,138 B2
(45) Date of Patent: Mar. 1, 2016

(54) DEVICE FOR TREATING TISSUE

(75) Inventor: Declan Soden, County Cork (IE)

(73) Assignee: UNIVERSITY COLLEGE CORK—NATIONAL UNIVERSITY OF IRELAND, CORK, Cork (IE)

( * ) Notice: Subject to any disclaimer, the term of this patent is extended or adjusted under 35 U.S.C. 154(b) by 729 days.

(21) Appl. No.: 13/395,242

(22) PCT Filed: Sep. 10, 2010

(86) PCT No.: PCT/IE2010/000053
§ 371 (c)(1),
(2), (4) Date: Mar. 9, 2012

(87) PCT Pub. No.: WO2011/030322
PCT Pub. Date: Mar. 17, 2011

(65) Prior Publication Data
US 2012/0172784 A1   Jul. 5, 2012

(30) Foreign Application Priority Data

Sep. 10, 2009   (IE) .................................... 2009/0688

(51) Int. Cl.
| | | |
|---|---|---|
| A61B 18/18 | (2006.01) |
| A61N 1/32 | (2006.01) |
| A61B 1/005 | (2006.01) |
| A61N 1/05 | (2006.01) |
| A61N 5/04 | (2006.01) |
| A61N 5/10 | (2006.01) |

(52) U.S. Cl.
CPC ................. *A61N 1/327* (2013.01); *A61B 1/005* (2013.01); *A61B 18/18* (2013.01); *A61N 1/0512* (2013.01); *A61N 5/04* (2013.01); *A61N 5/1002* (2013.01)

(58) Field of Classification Search
CPC ....... A61N 1/327; A61N 5/1002; A61N 5/04; A61N 1/0512; A61B 1/005; A61B 18/18
USPC .......................... 606/32–35, 41–45; 607/3, 88
See application file for complete search history.

(56) References Cited

U.S. PATENT DOCUMENTS

| 6,014,584 A * | 1/2000 | Hofmann et al. ................ 604/21 |
| 2002/0002372 A1 * | 1/2002 | Jahns et al. ...................... 606/41 |
| 2003/0216730 A1 * | 11/2003 | Barry et al. ...................... 606/45 |
| 2007/0179535 A1 * | 8/2007 | Morrissey et al. ................ 607/3 |
| 2009/0105662 A1 | 4/2009 | Levedusky |

FOREIGN PATENT DOCUMENTS

| WO | WO 2005/092433 | 10/2005 |
| WO | WO 2007/019321 | 2/2007 |
| WO | WO 2008/063478 | 5/2008 |

OTHER PUBLICATIONS

International Search Report dated Mar. 22, 2011.

* cited by examiner

*Primary Examiner* — Michael Peffley
*Assistant Examiner* — Amanda Zink
(74) *Attorney, Agent, or Firm* — Jacobson Holman, PLLC.

(57) ABSTRACT

An apparatus for use in carrying out a prophylactic or treatment procedure on tissue comprises a head piece 1 having a receiver 2 for receiving an instrument such as an endoscope 10 and chamber 3 into which tissue is drawn by vacuum. There are two electrodes 11 within the chamber 2 and two electrodes 25 located on opposite sides of the entrance 5 into the chamber. The voltage applied to the inner and outer electrodes 11, 25 can be varied independently an allows tissue underlying the device to be treated. This is particularly important for colorectal cancers.

8 Claims, 13 Drawing Sheets

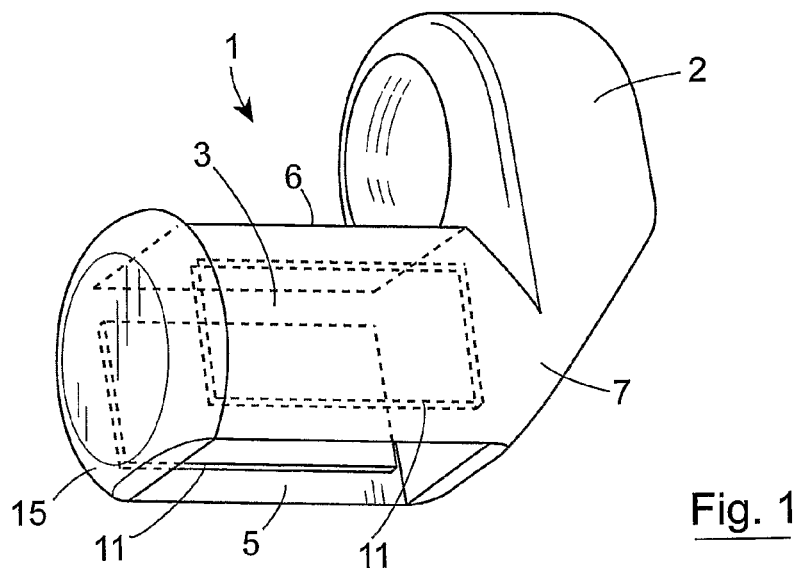
Fig. 1
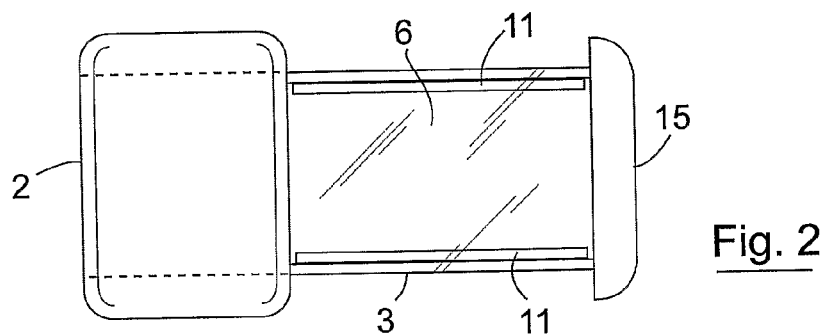
Fig. 2
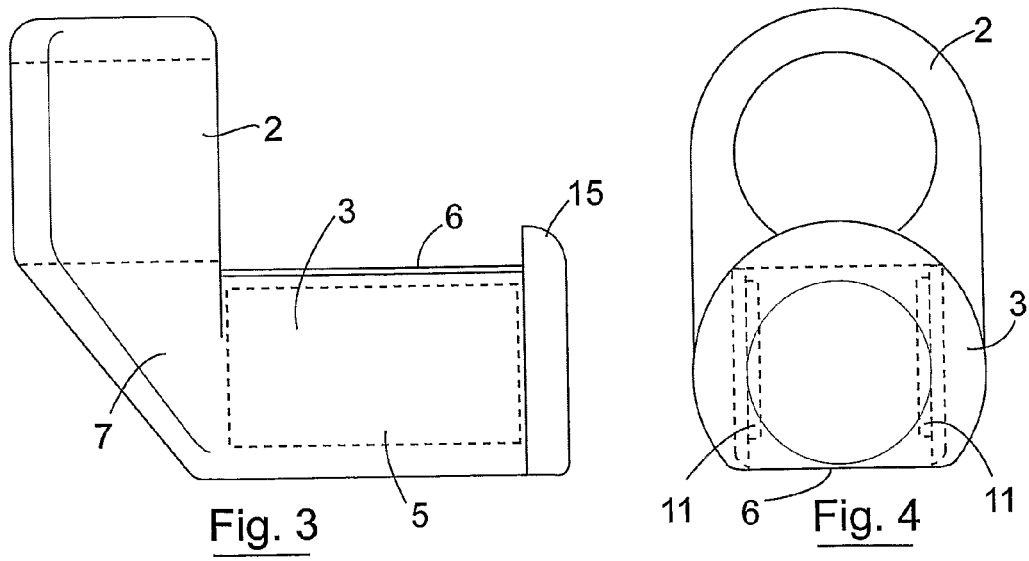
Fig. 3
Fig. 4

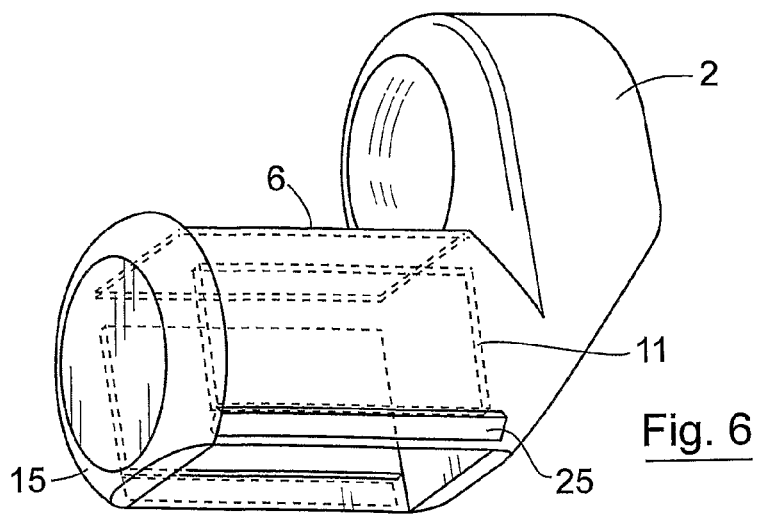
Fig. 6
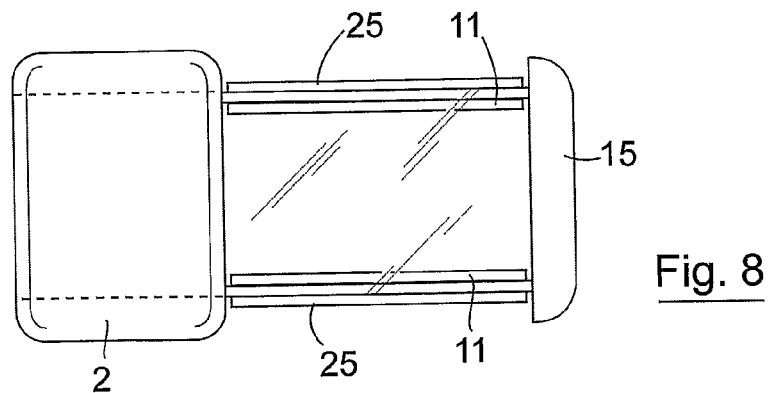
Fig. 8
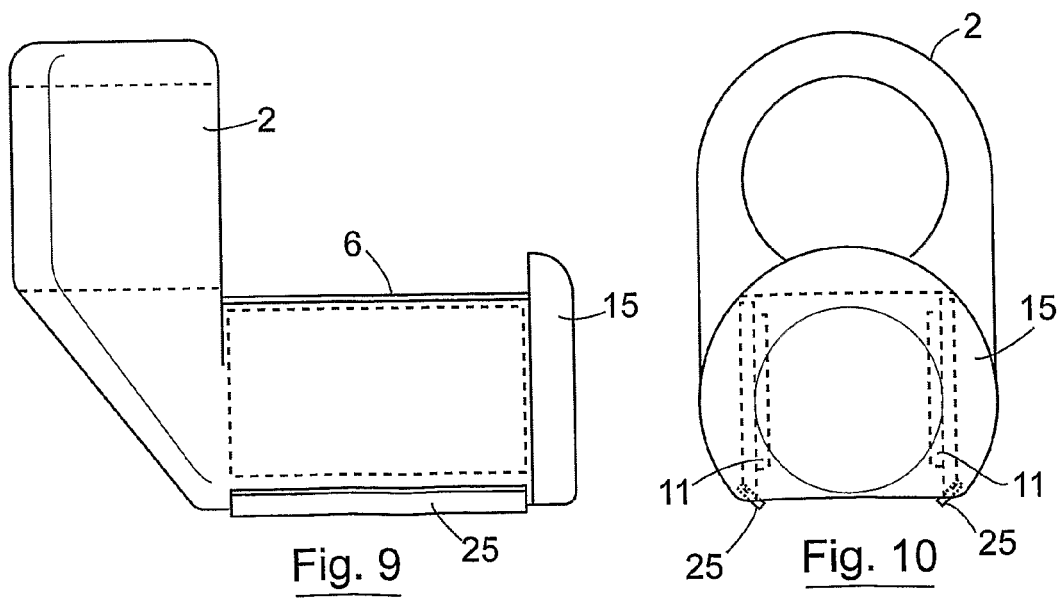
Fig. 9
Fig. 10

DEVICE FOR TREATING TISSUE

This is a national stage of PCT/IE2010/000053 filed Sep. 10, 2010 and published in English, which claims the priority of Irish number 2009/0688 filed Sep. 10, 2009, hereby incorporated by reference.

INTRODUCTION

This invention relates to devices and apparatus for use in carrying out prophylactic or treatment procedure on tissue. The invention also relates to a method of prophylaxis or treatment of tissue utilising a device or apparatus of the invention.

In our WO 2005/092433A we describe an apparatus for carrying out a prophylactic or treatment procedure on tissue comprising a device having a chamber and at least one active element such as an electrode within the chamber. The chamber has an opening through which tissue is drawn into the chamber. Means for drawing the tissue into the chamber may comprise a vacuum lumen with vacuum orifices in the chamber. Treatment such as electroporation may be applied to tissue in the chamber. The entire contents of WO 2005/092433A are herein incorporated by reference.

STATEMENTS OF INVENTION

According to the invention there is provided an apparatus for use in carrying out a prophylactic or treatment procedure on tissue comprising:—
- a head piece having a chamber with an entrance for receiving tissue;
- at least one first active element located within the chamber; and
- at least one second active element located externally of the chamber.

In one embodiment at least one first active element comprises an electrode.

In one case at least one second active element comprises an electrode.

There may be two first electrodes within the chamber. On one case the first electrodes are located on opposed sides of the chamber.

In one embodiment two second electrodes are provided outside of the chamber. The electrodes may be located on opposite sides of the entrance to the chamber.

In one embodiment the apparatus comprises means for applying electroporation to tissue located in the chamber.

In one case the apparatus comprises means for applying electroporation to tissue located outside of the chamber.

The apparatus in one embodiment comprises means for drawing tissue into the chamber. The means for drawing tissue into the chamber may comprise means for applying a vacuum to tissue. In one case the apparatus comprises a vacuum lumen for connecting the chamber in communication with a vacuum source. There may be one or more vacuum orifices for connecting the vacuum lumen in communication with the chamber.

In one case the vacuum source is configured to be located externally of a body.

In one embodiment the longitudinal axis of the vacuum lumen is offset radially from the longitudinal axis of the chamber.

The means for drawing tissue into the chamber may be configured to draw tissue towards the active element.

The means for drawing tissue into the chamber may be configured to draw tissue into contact with the active element.

In one case at least some of the active elements are the same.

In another case at least some of the active elements are different.

In one embodiment at least one active element has a therapeutic agent associated therewith. The active element may be impregnated with a therapeutic agent.

In one embodiment the apparatus comprises at least one sensor. The sensor may be used to monitor the treatment procedure. The sensor may be provided integral with an active element.

In one embodiment the device has at least one port to facilitate coupling of one or more ancillary devices. The ancillary device may comprise a needle for injecting a therapeutic agent into tissue.

In one embodiment the device is adapted for mounting to an instrument. The device may be adapted for mounting to a distal end of an instrument.

The instrument may comprise an endoscope, a laparoscope, a thoracoscope or a ureteroscope. In one case the instrument comprises a catheter.

In one embodiment the apparatus comprises a connector lumen for connecting the active element and/or the sensor in communication with a controller. The controller may be configured to be located externally of a body.

In one embodiment the first active element and the second active element are interconnected. The first active element and the second active element may be are integral. In one case the first and second active elements are formed by a single electrode.

In one embodiment the apparatus comprises a receiver for mounting an instrument such as an endoscope to the head piece. The receiver may be releasably mounted or mountable to the head piece.

In one case the chamber comprises a channel extending at least partially around the chamber for drawing a vacuum through the chamber, the channel having openings through which a vacuum is drawn. The openings may be spaced-apart around the chamber.

In one embodiment the apparatus comprises the head piece, a receiver for mounting an instrument to the headpiece, and a flexible joint or connection between the head piece and the receiver.

The invention also provides an instrument comprising an apparatus of the invention such as an endoscope, a laparoscope, a thoracoscope, an ureteroscope, and/or a catheter The invention further provides a method of prophylaxis or treatment of tissue comprising the steps of:—
- providing a device of the invention;
- delivering the device to a site of interest;
- drawing tissue into the chamber;
- applying treatment to the tissue drawn into the chamber using the at lease one first active element within the chamber;
- applying treatment to the tissue external of the chamber using the at least one second active element external of the chamber;
- releasing the tissue from the chamber; and
- withdrawing the device.

In one embodiment the tissue is drawn into the chamber by applying a vacuum. The tissue may be drawn towards the active element(s). The tissue may be drawn into contact with the active element(s).

In one case the method comprises the step of applying a stimulus to the tissue using the active element(s). The method may comprise the step of applying electrical energy and/or electromagnetic energy, and/or nuclear energy and/or heat energy via microwave or alternative energy source to the tissue.

In one embodiment the active element(s) comprises an electrode and the treatment applied to the tissue is an electroporation treatment.

In one case the tissue is a diseased tissue such as a tumour. The tumour may be oesophageal, colon, bladder, stomach, kidney, liver, pancreatic, fibrosarcoma, breast, prostate, glioma, lung, rectal, spleen, ovary, or melanoma type.

Alternatively, the tissue is a healthy tissue.

In one embodiment the method comprises the step of carrying out a further procedure on the tissue. The further procedure may be carried out before drawing tissue into the chamber. Alternatively or additionally the further procedure is carried out after drawing tissue into the chamber.

The further procedure may be a treatment procedure, and/or a visualisation procedure, and/or a drug treatment procedure, and/or a diagnostic procedure.

In one case the method comprises the step of coupling one or more ancillary laparoscopic devices to the device.

The method may comprise the step of injecting a therapeutic agent into the tissue.

In one case the device is mounted to or mountable to an instrument such as an endoscope, laparascope, thorascope, ureteroscope, and/or a catheter.

The device may be mounted to or mountable to a distal end of an instrument.

The method may comprise the step of monitoring the treatment procedure using a sensor.

The method may comprise the step of controlling the treatment procedure using a controller.

In one case the site of interest is a site on an external surface of a body. In another case the site of interest is an internal site within a body.

In a further aspect the invention provides a device for use in carrying out a prophylactic or treatment procedure on tissue comprising:—
  a head piece having a receiver for receiving an instrument and a chamber for receiving tissue wherein the receiver is offset from the chamber.

The chamber may be at least partially translucent.

In a further aspect the invention provides a device for use in carrying out a prophylactic or treatment procedure on tissue comprising:—
  a head piece having a receiver for receiving an instrument and a chamber for receiving tissue wherein the chamber is at least partially translucent.

In one embodiment the chamber comprises a front entrance and a rear wall opposite to the entrance, the rear wall being substantially translucent.

The chamber may be located distally of the receiver. In one case a longitudinal axis of the receiver is offset from the chamber entrance.

In one embodiment the head piece comprises a housing having a distal chamber portion and a proximal receiver portion. A longitudinal axis of the chamber portion may be offset from a longitudinal axis of the receiver portion. The housing may have a bend intermediate the chamber portion and the receiver portion.

In one embodiment the head piece comprises a tapered distal tip. The distal tip may be rounded.

In one case the proximal receiver portion is shorter than the distal chamber portion of the housing. The length of the proximal receiver portion may be less than 50% of the length of the distal chamber portion.

The invention further provides an apparatus for carrying out a prophylactic or treatment procedure on tissue comprising:—
  a device of the invention;
  at least one active element within the chamber;
  means for drawing tissue into the chamber; and
  means for applying a treatment to tissue drawn into the chamber.

The means for drawing tissue into the chamber may comprise means for applying a vacuum to tissue. In one case the apparatus comprises a vacuum lumen for connecting the chamber in communication with a vacuum source. The apparatus may comprise one or more vacuum orifices for connecting the vacuum lumen in communication with the chamber.

In one case the vacuum source is configured to be located externally of a body.

The longitudinal axis of the vacuum lumen may be offset radially from the longitudinal axis of the chamber.

The means for drawing tissue into the chamber may be configured to draw tissue towards the active element. The means for drawing tissue into the chamber may be configured to draw tissue into contact with the active element.

In one case the active element comprises an electrode.

The means for applying treatment may comprise means for applying electroporation to tissue in the chamber.

In one case the active element comprises a conductive element.

The active element may comprise an optical element and/or a radiation source and/or an ultrasound source.

The apparatus may comprise at least two active elements.

At least some of the active elements are the same. Alternatively at least some of the active elements are different.

In one embodiment at least one active element has a therapeutic agent associated therewith. The active element may be impregnated with a therapeutic agent.

The location of the active elements in the chamber may be configured to minimise the variation in intensity of the physical field within the chamber.

In one embodiment the apparatus comprises
  at least one first active element located within the chamber; and
  at least one second active element located externally of the chamber.

At least one first active element may comprise an electrode.

At least one second active element may comprise an electrode.

There may be two first electrodes within the chamber. The first electrodes may be located on opposed sides of the chamber.

In one case there are two second electrodes outside of the chamber. The electrodes may be located on opposite sides of the entrance to the chamber.

The apparatus may comprise means for applying electroporation to tissue located in the chamber and/or means for applying electroporation to tissue located outside of the chamber.

The apparatus may comprise at least one sensor. The sensor may be used to monitor the treatment procedure.

The sensor may be provided integral with the active element.

In one embodiment the head piece has at least one port to facilitate coupling of an ancillary device to the head piece.

The ancillary device may comprise a needle for injecting a therapeutic agent into tissue.

In one embodiment the apparatus comprises an instrument located in the receiver. The instrument may comprise an endoscope, a laparoscope, a thoracoscope, a ureteroscope and/or a catheter.

In one case the apparatus comprises a connector lumen for connecting the active element and/or the sensor in communication with a controller. The controller may be configured to be located externally of a body.

In a further aspect the invention provides a device for use in carrying out a prophylactic or treatment procedure on tissue comprising:— a head piece having a chamber for receiving tissue wherein the head piece is at least partially flexible for navigating tortuous passageways and/or obstructions.

In one case the head piece is of a flexible material. The head piece may be of a foam material.

In one case the head piece is of a polyurethane material.

The device may comprise at least one active element. The active element may be flexible to conform with the head piece. In one case the active element comprises an electrode.

BRIEF DESCRIPTION OF THE DRAWINGS

The invention will be more clearly understood from the following description of some embodiments thereof, given by way of example only, with reference to the accompanying drawings, in which:

FIG. 1 is a perspective view of a head piece for use in carrying out a prophylactic or treatment procedure on tissue;

FIG. 2 is a top plan view of the head piece of FIG. 1;

FIG. 3 is a side elevational view of the head piece;

FIG. 4 is an end view of the head piece;

FIG. 6 is a perspective view of another head piece according to the invention;

FIGS. 8, 9 and 10 are respectively top plan, side elevational and end views of the head piece of FIGS. 6 and 7;

DETAILED DESCRIPTION

Figure 5:
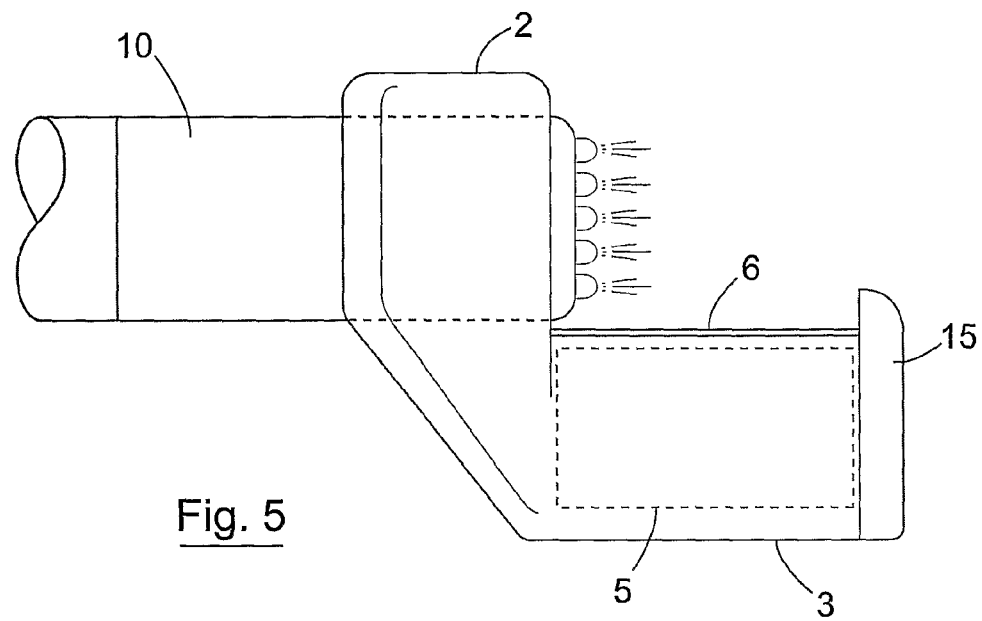
FIG. 5 is an elevational view of the head piece with an endoscope in position.
Figure 7:
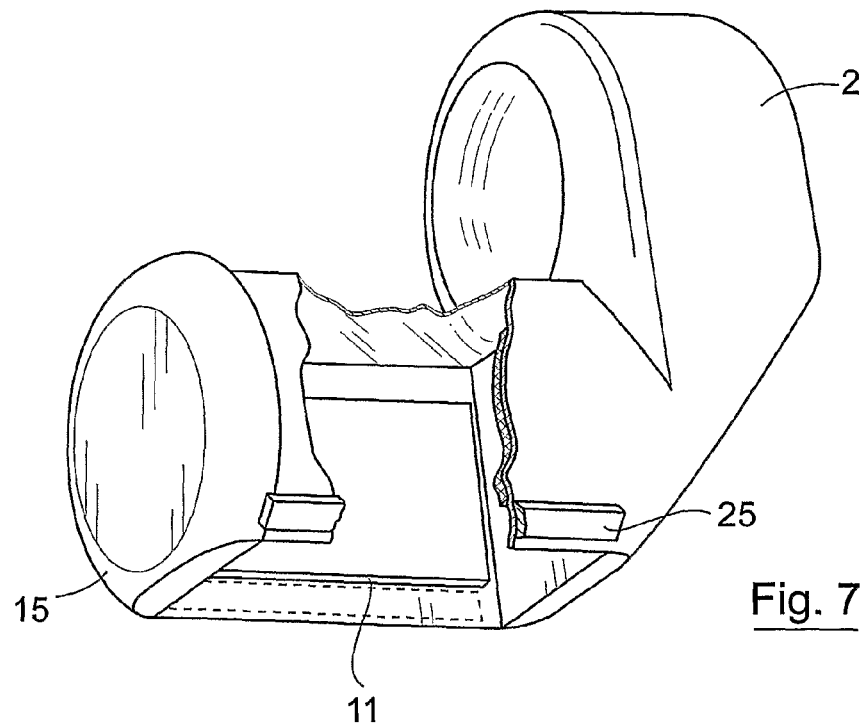
FIG. 7 is a perspective, partially cut-away view of the head piece of FIG. 6.

Referring to the drawings and initially to FIGS. 1 to 5 thereof there is illustrated an apparatus according to the invention which is suitable for carrying out a prophylactic or treatment procedure on tissue.

The apparatus comprises a head piece 1 having a receiver 2 for receiving an instrument such as an endoscope 10 and a chamber 3 for receiving tissue. It will be noted that the receiver 2 is offset from the chamber 3. The chamber 3 is at least partially translucent to facilitate visualisation of the chamber 3 using the endoscope 10.

In this case the chamber 3 comprises a front entrance 5 and a rear wall 6 opposite to the entrance 5. The rear wall 6 is translucent and may for example, be of a suitable translucent plastics material.

The chamber 3 is located distally of the receiver 2. Longitudinal axes through the receiver 2 and chamber 3 are offset and there is a bend or transition region 7 between the receiver 2 and the housing 3. The overall length of the head piece is minimised.

The device has a number of active treatment elements. In this case there are two active treatment elements in the form of planar electrodes 11 on opposite sides of the chamber 3. The device also has a vacuum lumen (not shown) for drawing tissue into the chamber 3 through the entrance 5. A vacuum is applied through the vacuum lumen to apply a vacuum to tissue and to draw the tissue into the chamber 5 and into contract with the electrodes 11.

In this case each active element is provided in the form of a rigid planar member fixedly attached to the interior wall of the chamber 5. Each active element comprises an electrode 11 for applying an electroporation treatment to tissue drawn into the chamber 5.

In use, the head piece is mounted to an instrument 10 and the instrument 10 is advanced to a desired site of interest within the body. A vacuum is then applied using a vacuum source externally of the body. The vacuum draws the tissue into the chamber 3 and into contact with the active elements 11. When tissue is drawn into the chamber 3 a surgeon can see it through the rear wall 6 and can confirm appropriate engagement with the tumour.

The electrodes 11 are used to apply an electroporation treatment to the tissue in the chamber 3.

The device attaches to the head of an endoscope 10 and draws tumour tissue into a chamber 3 under vacuum pressure. An electrical field is generated around the tumour which ensures the tissue becomes porous. A therapeutic agent such as a chemotherapeutic macromolecule, for example bleomycin may then be delivered to the tissue. The device may incorporate a local injector such as one or more needles to deliver the therapeutic agent to the tissue. Thus, passive diffusion of a locally present therapeutic agent is facilitated. Absorption occurs only in the area that has been electroporated and therefore is targeted to the tumour, leaving surrounding healthy tissues unaffected. One of the significant advantages of the system is that healthy cells and tissues surrounding the tumour can be treated to a greater degree that conventional ablation methods e.g. radiotherapy and radiofrequency ablation.

Some advantages of the invention are:

speed of application: pulses are delivered in 1 msec;

targeted delivery: drug adsorption is localised to the area treated by the device, only a fraction of drug used compared to standard (therefore less side effects for patient);

healthy tissue: studies to date indicate that healthy tissue is significantly less affected than tumour tissue allowing wider margins around the tumour to be treated, thereby decreasing the potential risk of recurrence;

repeatable: treatment can be delivered multiple times if required;

minimally invasive and non-toxic: the dose of drug is less than 1% of that used in conventional chemotherapy—endoscopic application allows for a greater number of patients to receive treatment;

unlike ablation methods the method of cell death is apoptotic, not an inflammatory, necrotic response;

new therapeutics: future potential for the device to be used for gene therapy;

the endoscopic application and electroporation treatment can be applied with the patient under sedation and can be completed on an outpatient basis;

the technology is complementary to existing therapies, is easy to perform and is relatively inexpensive;

many solid tumours may be accessed through body orifices without the need for surgical intervention.

The invention provides an endoscopic attachment for use in the minimally invasive treatment of gastrointestinal cancers such as colorectal and oesophageal cancers. Colorectal cancer is not adequately addressed by existing therapies. Oesophageal cancer is the fastest growing cancer in the western world and 60% of patients are deemed unsuitable for surgical treatment. The device of the invention can however be used to treat such tumours. In clinical practice an electric field is applied to the tumour followed by the delivery of electroporation pulses. The treatment duration is approximately 1 msec per application, which is significantly quicker than radiofrequency ablation or other thermal ablation methods.

During the treatment procedure, sensors may be used to enable the user to monitor the progress of the treatment procedure. The progress of the treatment procedure may be controlled using the controller.

When the treatment procedure is completed the vacuum is released to release the tissue from within the chamber 3 and the apparatus is retrieved from the body by withdrawing the instrument 10.

A further procedure may be carried out on the tissue before and/or after drawing tissue into the chamber 3. Possible further procedures include a treatment procedure, a visualisation procedure, a drug treatment procedure, or a diagnostic procedure.

The apparatus of the invention is suitable for treating a diseased tissue, such as a tumour. The tumour may be oesophagal, colon, bladder, stomach, kidney, liver, pancreatic, fibrosarcoma, breast, prostate, giloma, lung, rectal, spleen, ovary or melanoma type.

The apparatus of the invention is also suitable for carrying out a prophylactic treatment on healthy tissue.

The site of interest may be an internal site within body, or an external site on an external surface of the body.

The location of the active elements 11 within the chamber 5 is chosen to minimise the variation in intensity of the electric field within the chamber 5. In this manner, the device achieves a substantially homogenous physical field throughout the chamber 5.

A distal end 15 of the device is substantially rounded. In this way the device defines a smooth crossing profile.

The apparatus may be mounted to an instrument for delivery to a site of interest in a body and subsequent retrieval from the body. Typically the apparatus will be mounted to the distal end of an instrument. Suitable instruments to which the apparatus may be mounted include an endoscope, a laparoscope, a thoracoscope, a ureteroscope, a catheter.

Referring to FIGS. 6 to 10 there is illustrated another apparatus according to the invention which is similar to the device of FIGS. 1 to 5 and like parts are assigned the same reference numerals.

In this case there is at least one first active element such as an electrode 11 located within the chamber 3 and at least one second active element located externally of the chamber. In this instance there are two second electrodes 25 located on opposite sides of the entrance 5 into the chamber 3. The additional electrodes 25 on the outside of the chamber 3 improve the electrical field distribution. The voltage applied to the inner and outer electrodes can be varied independently. For example, to optimise field distribution the voltage applied to the outer electrodes 25 may be about three times larger than the voltage applied to the inner electrodes 11. The outside electrodes 25 may be of any suitable shape.

In the device described with reference to FIGS. 1 to 5 the electrical field generated by the device with two plate parallel electrodes 11 contained within the device is largely kept within the chamber. However with two additional electrodes 25 (wired separately) and placed on the outside of the chamber as illustrated in FIGS. 6 to 10 (somewhat like a pair of skis) a larger volume of tissue can be treated by targeting the tissue underlying the device. This would be particularly suitable for colorectal cancers.

Figure 11:
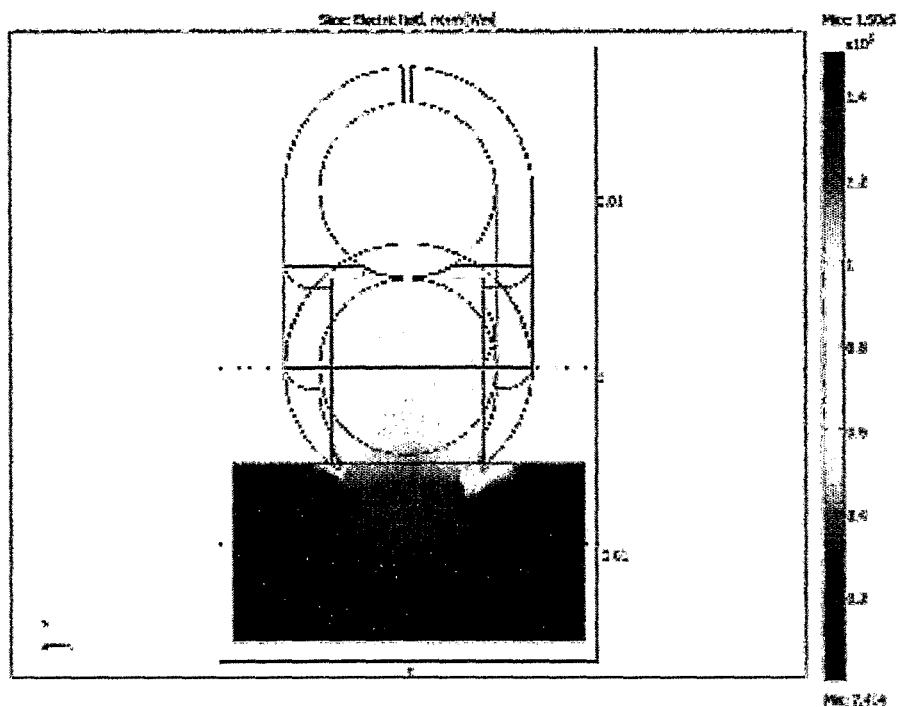
FIGS. 11 and 12 are diagrams illustrating the electrical field generated using the device.
Figure 12:
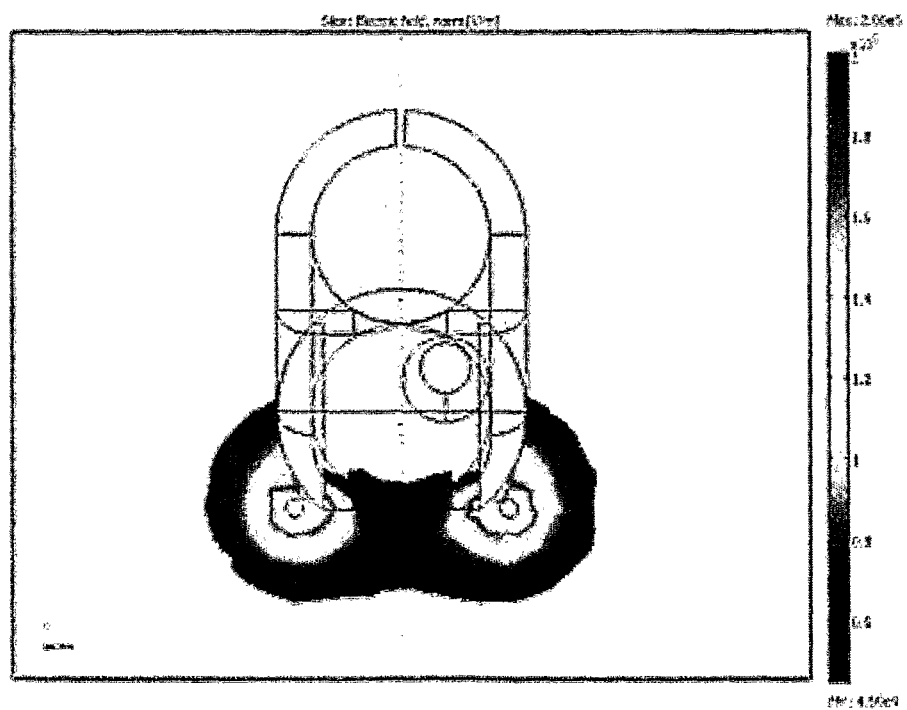
Figure 13:
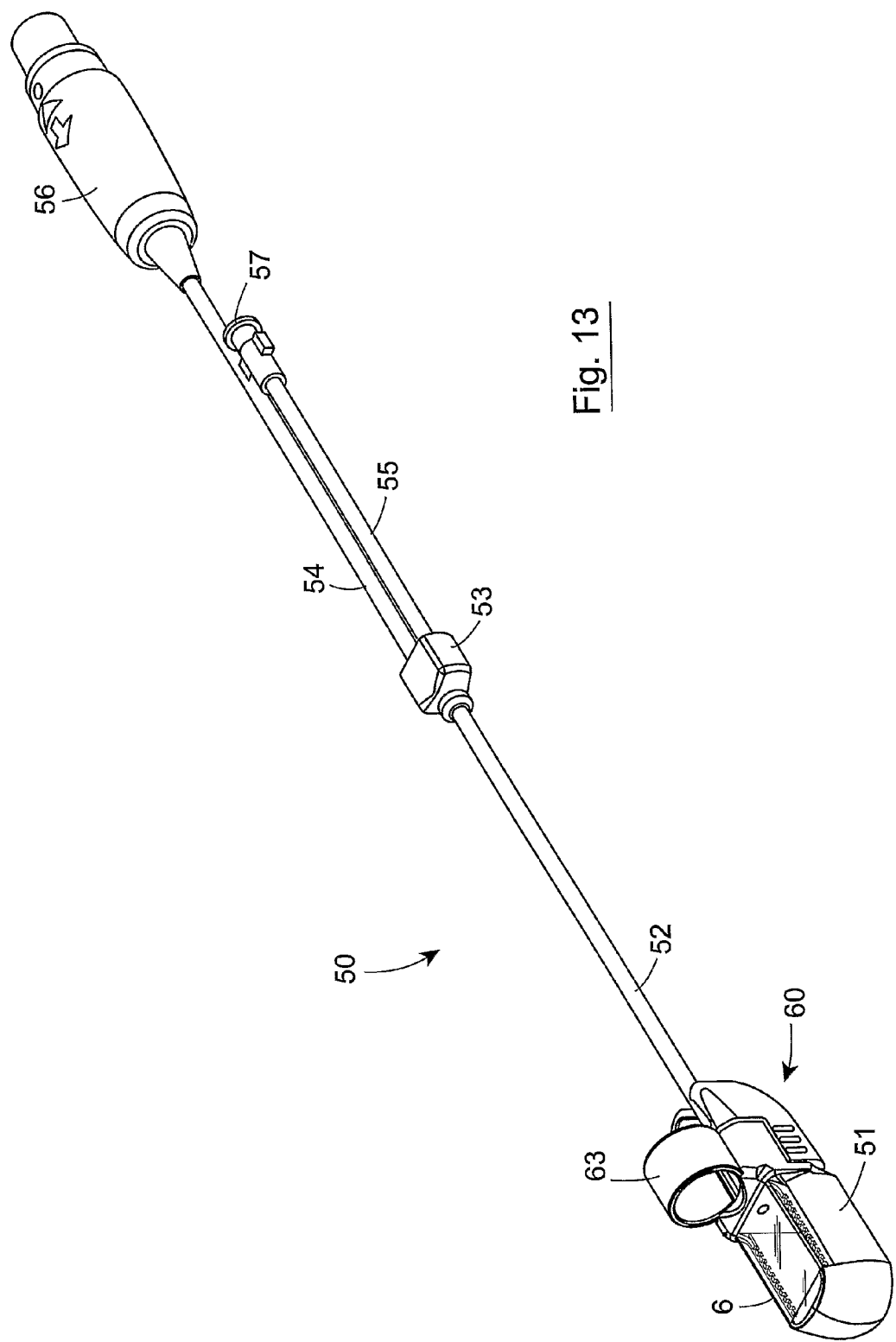
FIG. 13 is a perspective view of a device according to the invention attached to an operating shaft.
Figure 14:
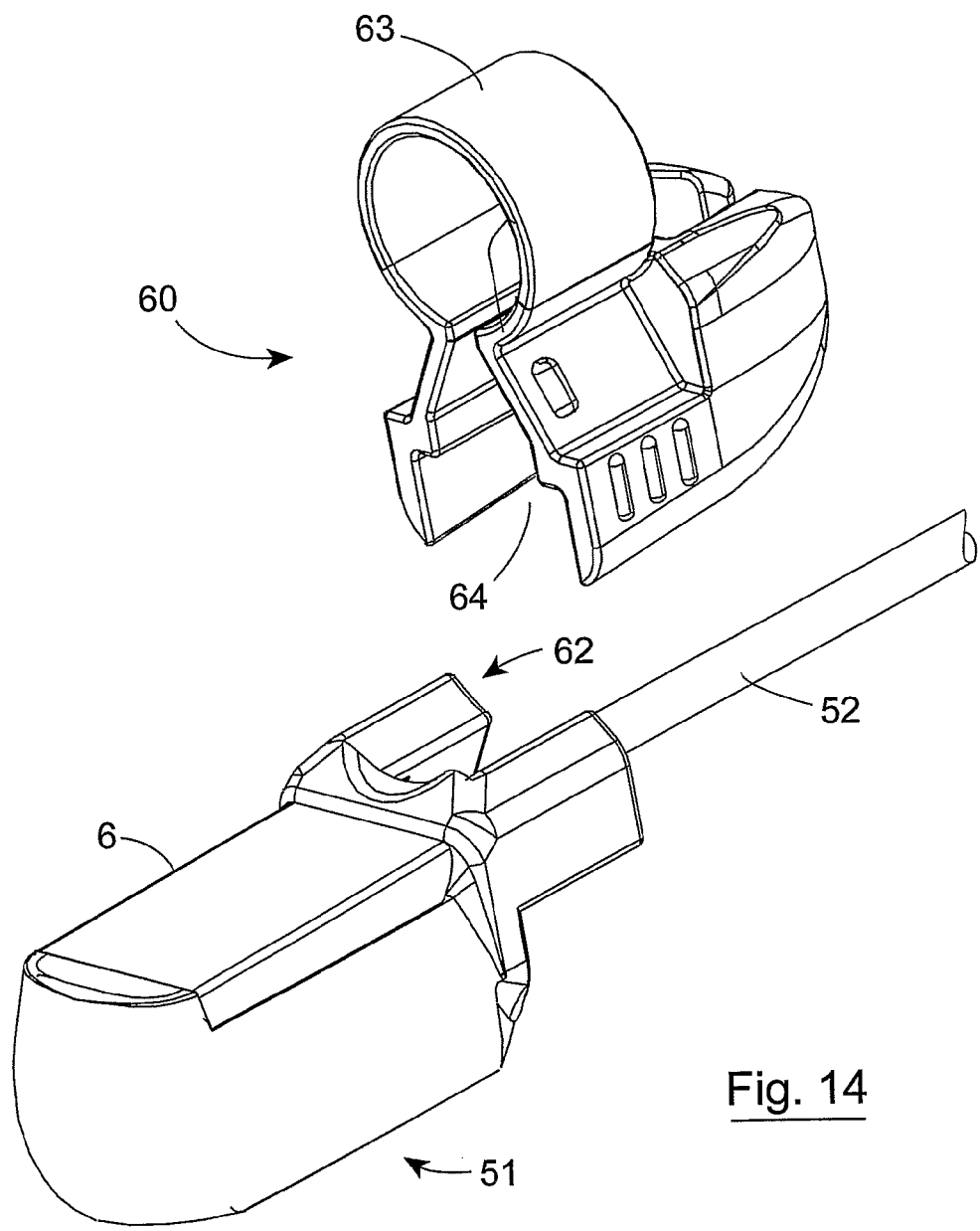
FIG. 14 is an exploded view of part of the device of FIG. 13.
Figure 15:
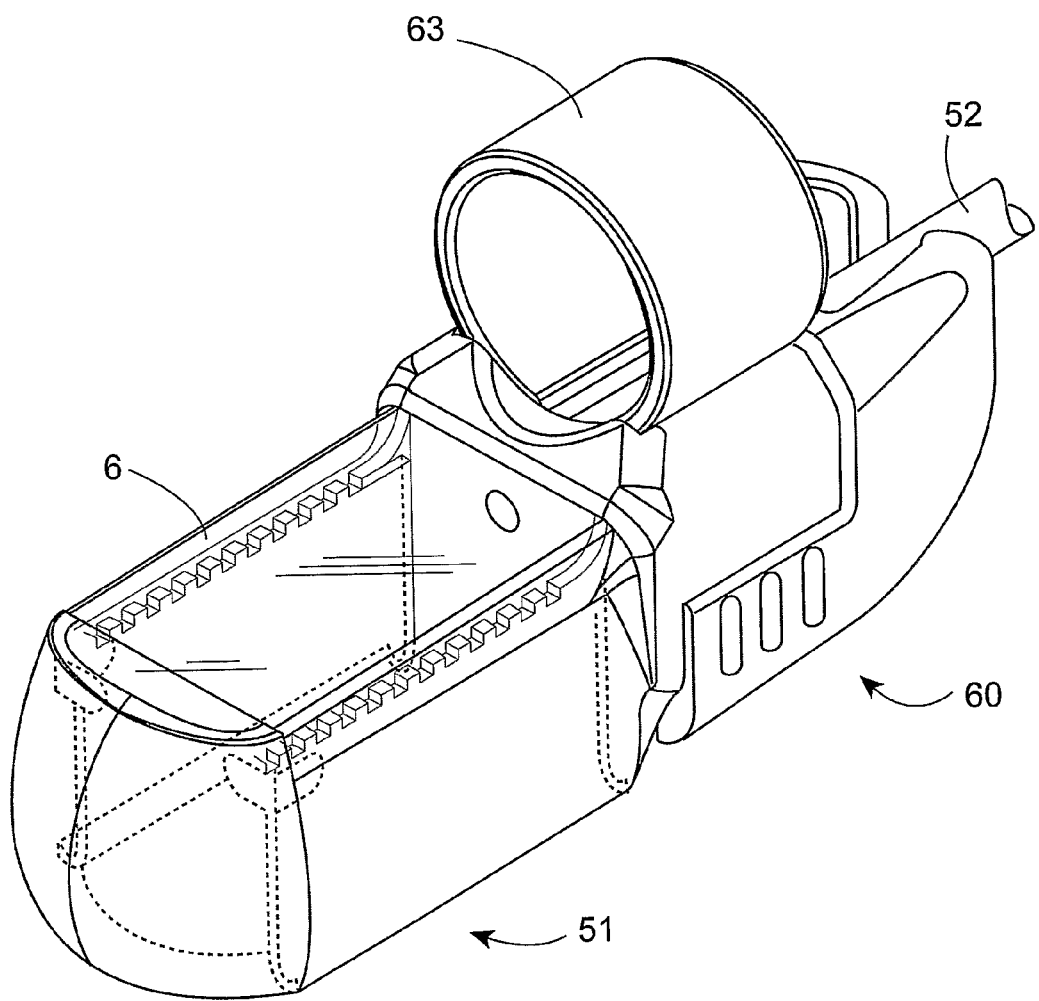
FIG. 15 is an enlarged perspective view of a head part of the device of FIGS. 13 and 14.
Figure 16:
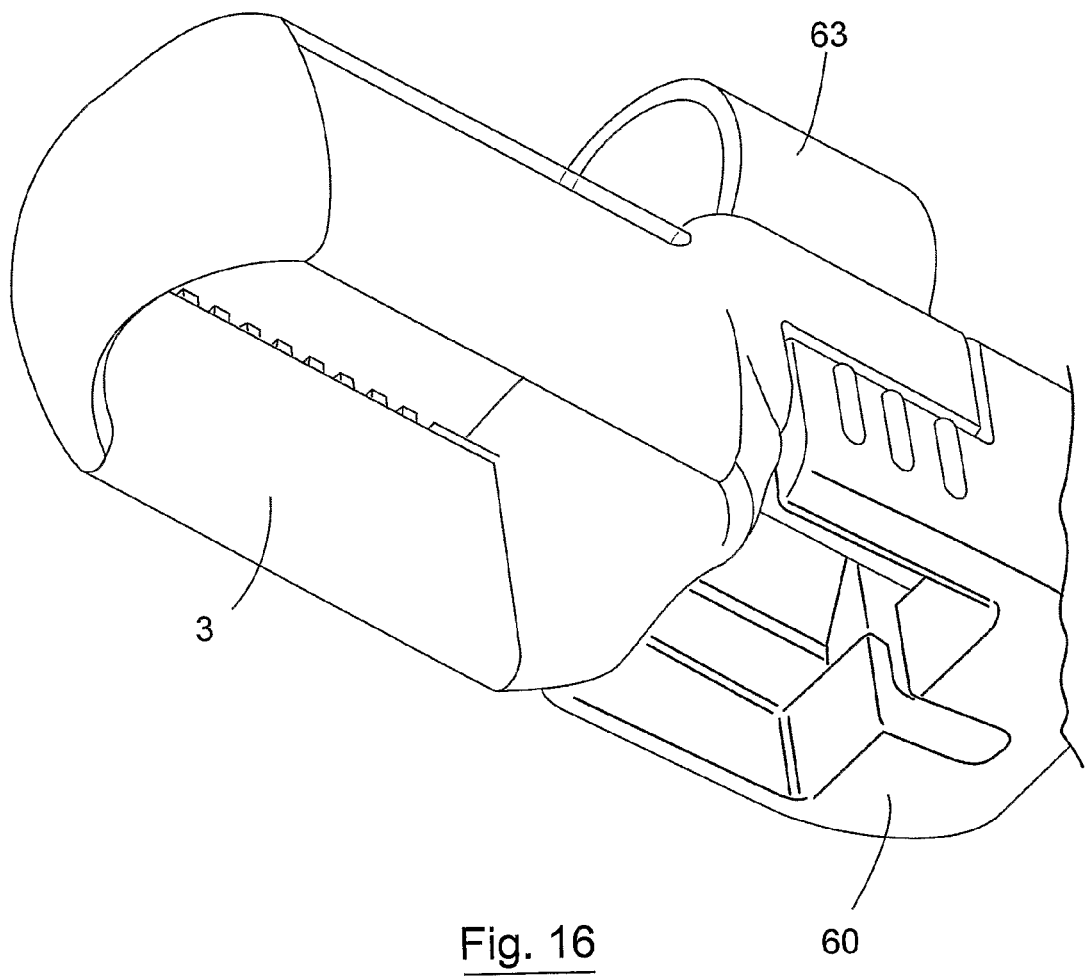
FIG. 16 is a perspective view of the underside of the head part.
Figure 17:
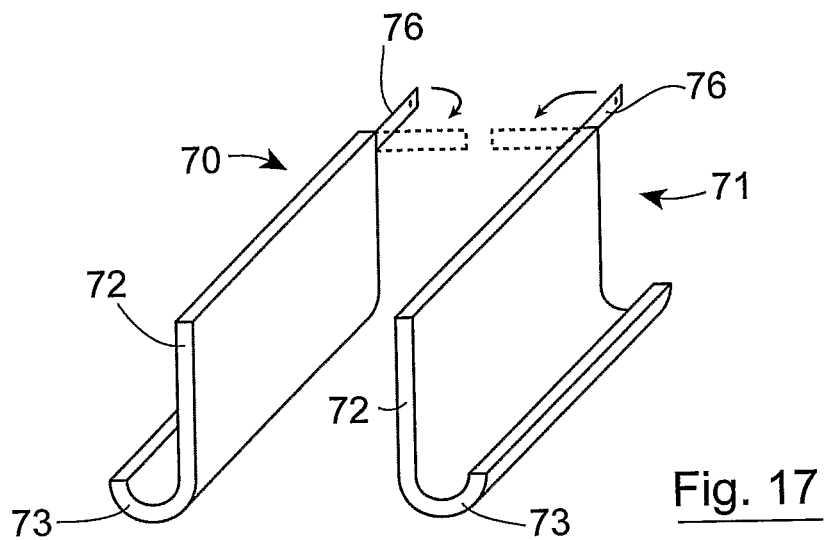
FIG. 17 is a diagram of part of the head piece of the device showing vacuum flow.
Figure 18:
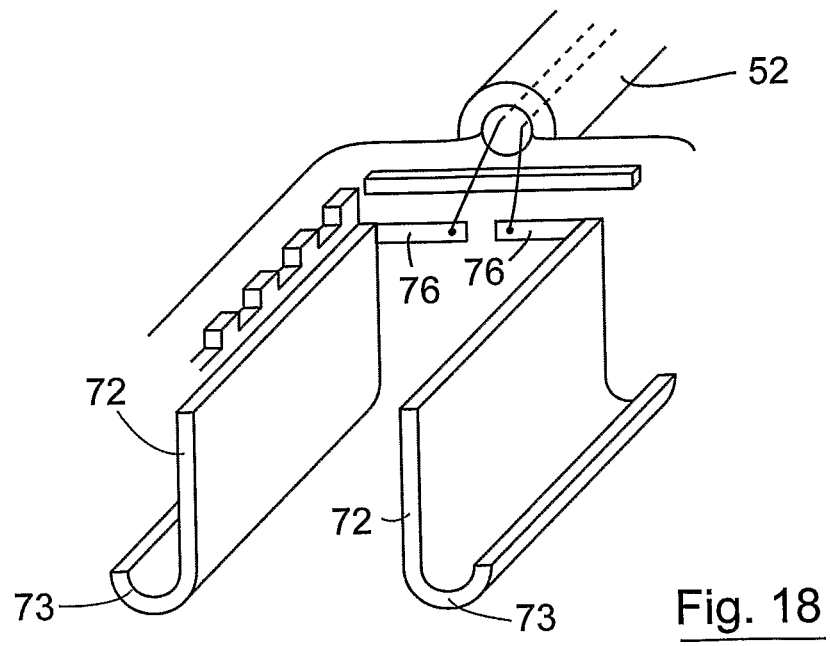
FIG. 18 is a perspective view of electrodes for a head piece.
Figure 19:
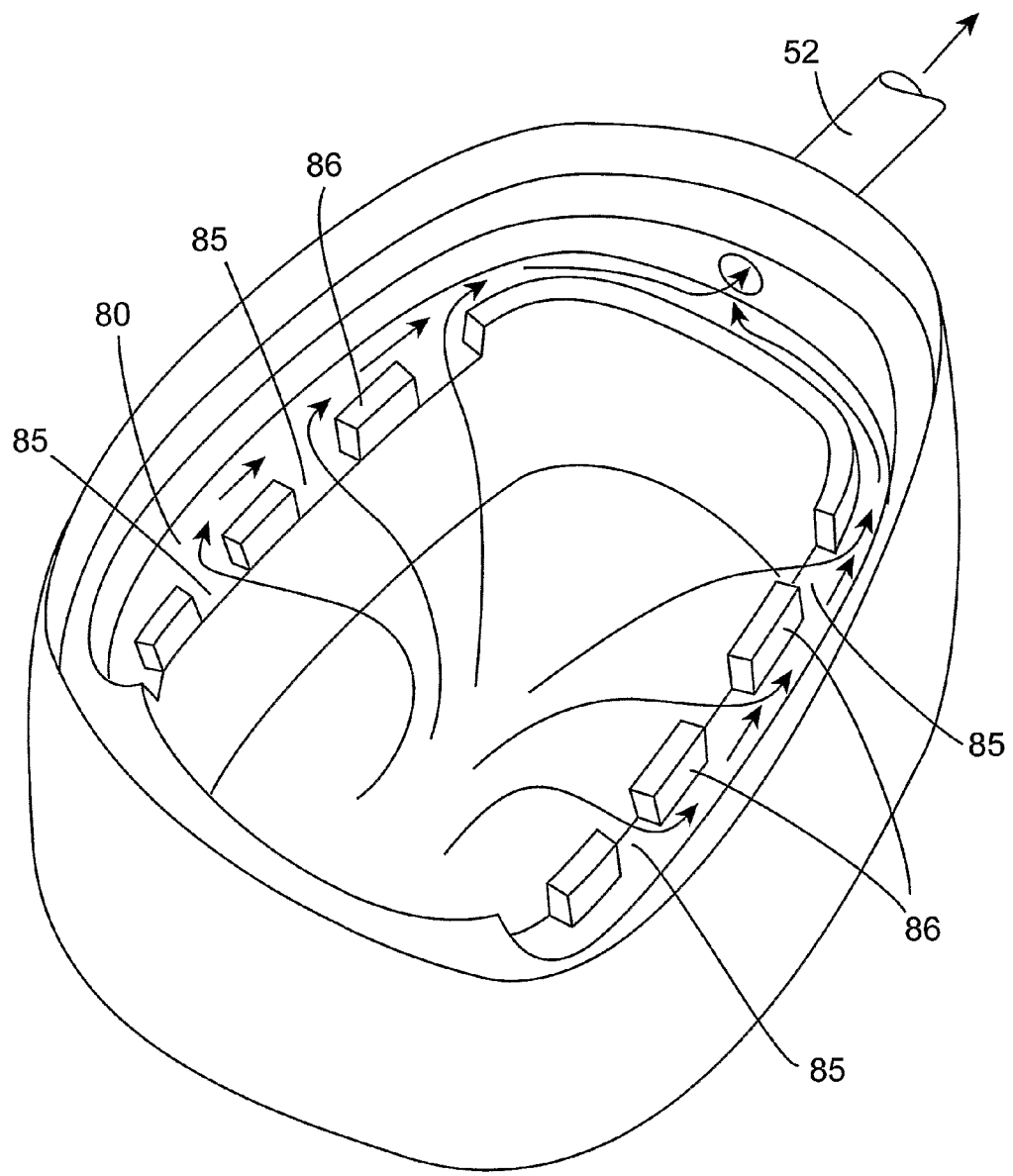
FIG. 19 is a partial view of the electrodes of FIG. 18 in position in a head piece.

Referring to FIGS. 11 and 12 the electric field generated by a device with inner chamber electrodes (FIG. 11) and with outer electrodes (FIG. 12) for deeper tissue penetration is illustrated. In (FIG. 11) with the electrodes 11 positioned parallel on both sides of the vacuum chamber, the electric field distribution inside is almost completely homogenous. The electric field is mostly limited to the chamber itself and does not protrude more than a few millimeters outside. Typically, 5 mm outside the chamber the electric field is ten times less than in the middle of chamber. With the electrodes 25 placed external of the device a field is generated which is dependent on the voltage applied and is capable of effectively electroporating tissue lying under the device.

The standard electroporation pulse parameters employed are typically in the region of at least 0.1 msec and up to several msec in length and with a frequency of at least 1 Hz. Standard electroporation typically consists of eight 0.1 msec pulses for a single treatment application to facilitate drug delivery.

The voltage applied for skin based application is in the range of 1000 to 13000 v/cm. For intraluminal application the required voltage can be reduced to under 1000 v/cm but typically should be greater than 500 v/cm.

In this device we have the possibility to apply two distinct electroporation pulse parameters to the tissue within the chamber and positioned directly under the chamber. In the first instance an electrical pulse is delivered between the two plate electrodes 11 of a specific voltage, pulse length and frequency. In the second instance a higher or lower voltage, pulse length and frequency can be applied to the external electrodes 25 which can be determined by the depth of tissue the clinician/operation intends to treat. A higher voltage will increase the surface area affected by the electrical field but will be allowable up to a maximum voltage that has been determined not to cause significant necrotic damage to tissue surrounding the electrode or to the patient.

Referring to FIGS. 13 to 19 there is illustrated another device 50 according to the invention, in which parts similar to those described in other drawings are assigned the same reference numerals. The device 50 comprises a head piece 51 with a conduit 52 extending therefrom. The conduit 52 provides a lumen for passage of vacuum and electrical connections. The conduit 52 is connected to a junction 53 which has a first and second conduits 54, 55 extending therefrom. The first conduit 54 leads the electrical connectors to a distal connector 56 for connection with a source of electrical power. The second conduit 55 has a distal port 57 for connection to a vacuum source. It will be appreciated that these aspects in particular may be utilised with any of the head pieces described herein.

The head piece 51 of the device 50 is releasably mounted to a receiver 60 for an endoscope. The receiver 60 is releasably mounted, in this case by connections 62, 64, (such as tongue and groove and/or snap fit projections) to the head pieces 51. The receiver comprises a ring element 63 into which an endoscope is mounted. The ring element 63 may be of a flexible material to facilitate mounting of an endoscope. By providing a range of receivers 60 a wide range of different endoscopes can be mounted to the headpiece 51. This greatly enhances the application of the device to a wide range of different endoscopes. Again, this aspect can also be applied to any of the headpiece designs described herein.

Figure 20:
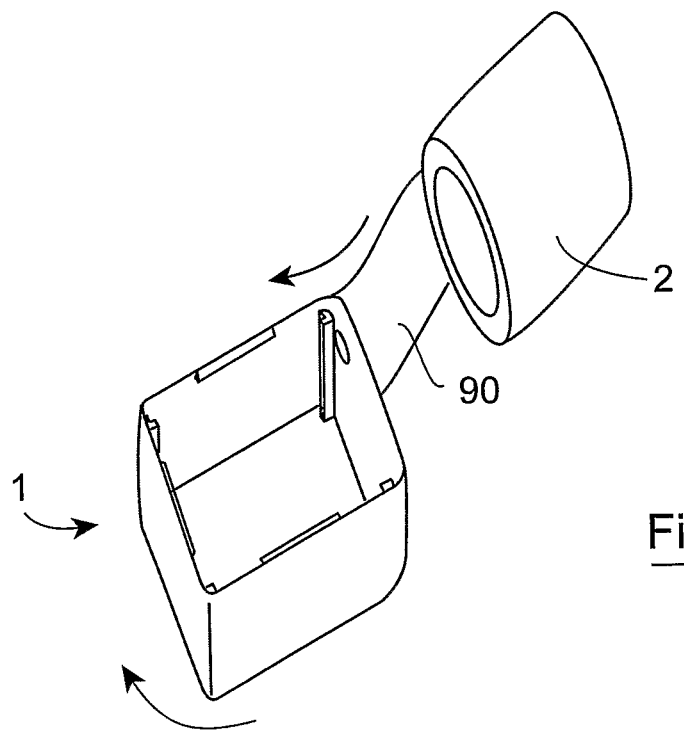
FIGS. 20 and 21 are diagrams of another device of the invention.
Figure 21:
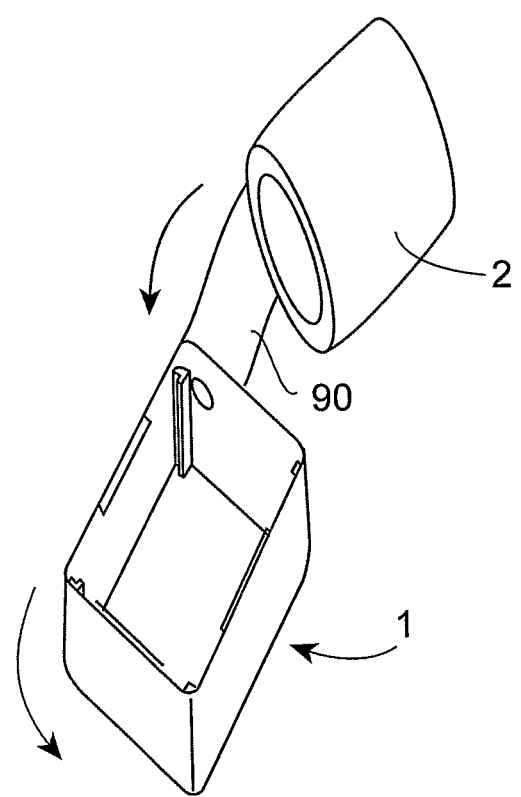
Figure 22:
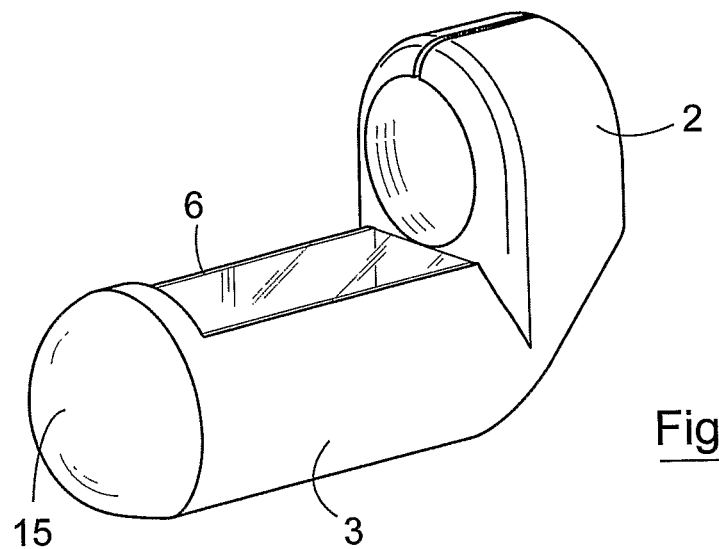
FIGS. 22 to 26 are perspective views of other head pieces.
Figure 23:
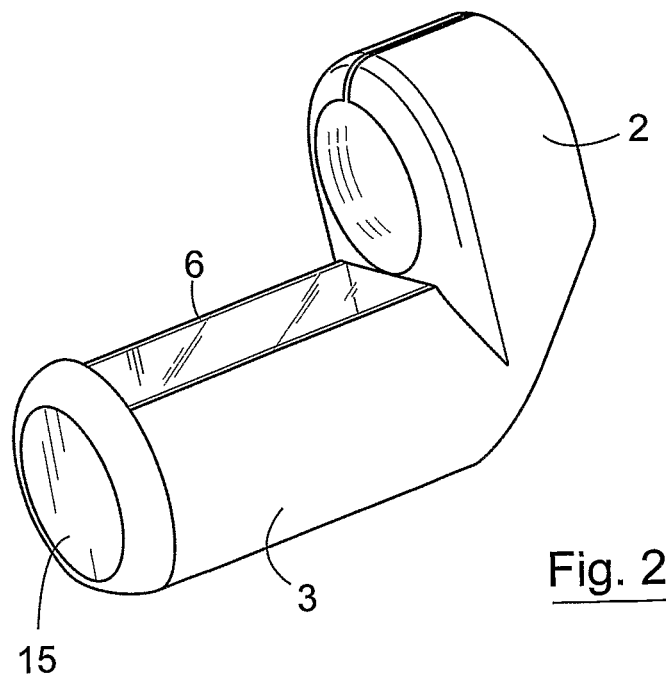
Figure 24:
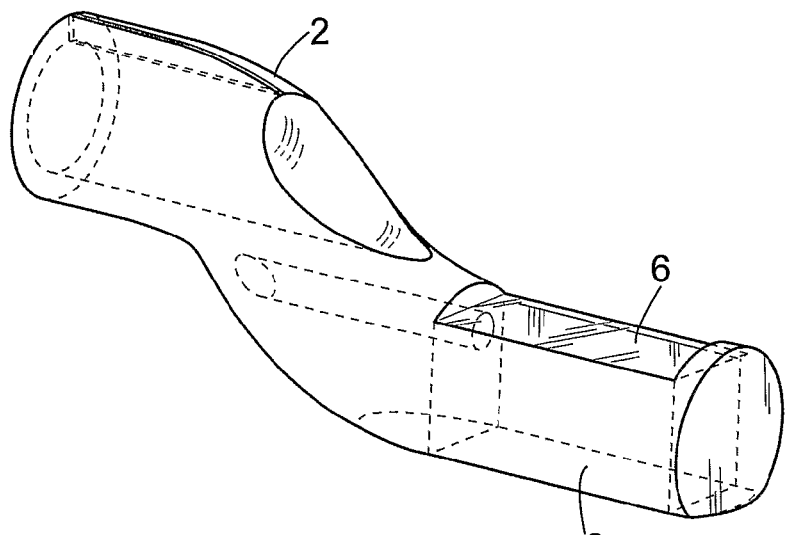
Figure 25:
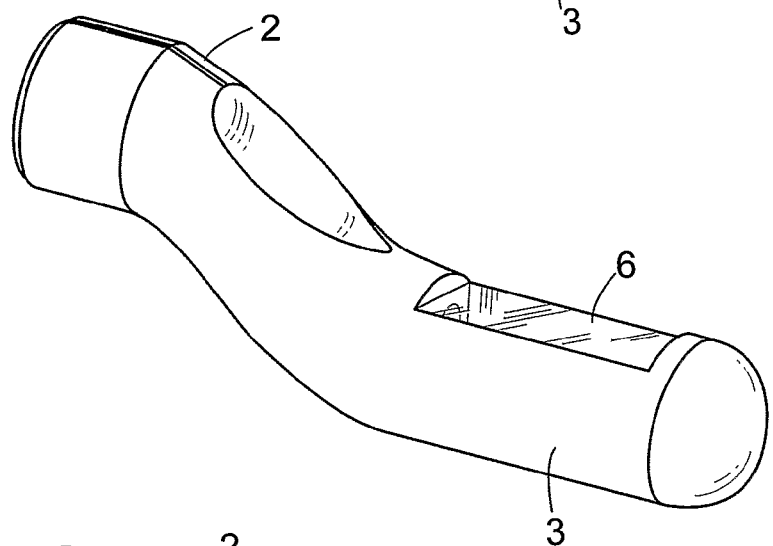
Figure 26:
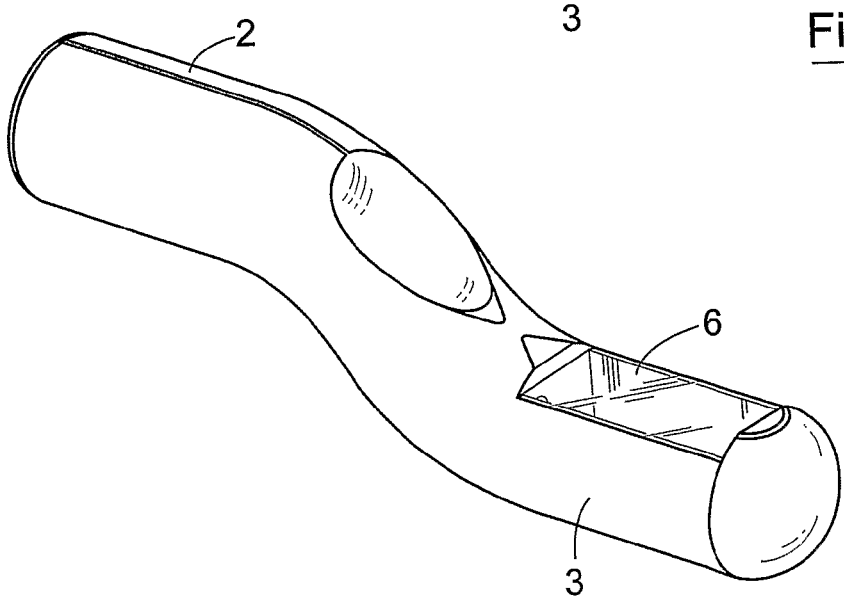

Referring in particular to FIGS. 20 and 21 in this case there are two electrodes 70, 71 each of which comprises a planar part 72 which is located within the chamber of the headpiece 51 and an out-turned lip part 73 which extends around the edge of the chamber so that portions of the electrodes are external to the chamber. This is similar to the arrangement of the skid-type electrodes described with reference to FIGS. 5 to 11. The lipped electrodes 70, 71 can be used in situations where it is not necessary to independently vary the power supplied to internal and external electrodes.

The electrodes 70, 71 have bendable tabs 76 for ease of mounting and electrical connection.

FIGS. 13 to 19 also illustrate another aspect which may be applied to any of the devices described herein. The vacuum is drawn on the chamber through an inlet channel 80 which extends from the vacuum lumen around the back and side walls of the chamber. The chamber has a plurality of exit openings 85 into the vacuum channel 80 to distribute the applied vacuum around the chamber and thereby reducing the risk of the vacuum path becoming blocked, in use. In this case the openings 85 are defined between castellations 86. Each individual opening 85 also provides a filter to prevent larger debris from being drawn into the vacuum line. The arrangement also facilitates even sealing/filling of the chamber with tissue as vacuum is acting on the tissue from a plurality of locations around the chamber.

The device can be at least partially flexible for navigating tortuous passageways and/or obstructions. One example is illustrated in FIGS. 20 and 21. For example, such a device could be used to navigate around bends such as the epiglottis. The device may include a flexible joint 90. The joint may comprise a flexible material, for example a foam material such as polyurethane.

FIGS. 22 to 26 illustrate various alternative head pieces which are similar to those described above and like parts are assigned the same reference numerals. Whilst there are some advantages associated with these head pieces in general they are not as advantageous as those of the devices of FIGS. 1 to 10 in terms of size, profile and/or visualisation.

It will be appreciated that various features described and/or illustrated with reference to an embodiment of the invention can be readily used in any of the other embodiments.

The invention is not limited to the embodiments hereinbefore described, with reference to the accompanying drawings, which may be varied in construction and detail.

The invention claimed is:

1. An apparatus for use in carrying out a prophylactic or treatment procedure on tissue comprising:—
   a head piece having a tissue treatment chamber with an entrance for receiving tissue and electrodes for applying electroporation to tissue;
   the electrodes comprising two internal electrodes located within the chamber on opposed sides of the chamber and two external electrodes located externally of the chamber and on opposite sides of the entrance to the chamber, the external electrodes being electrically separated so that the voltage, pulse length and/or frequency applied to the internal electrodes and the external electrodes are variable independently.

2. The apparatus as claimed in claim 1 comprising a vacuum lumen for connecting the chamber in communication with a vacuum source.

3. The apparatus as claimed in claim 1 wherein the longitudinal axis of the vacuum lumen is offset radially from the longitudinal axis of the chamber.

4. The apparatus as claimed in claim 1 wherein the chamber comprises a channel extending at least partially around the chamber for drawing a vacuum through the chamber, the channel having openings through which a vacuum is drawn.

5. The apparatus as claimed in claim 1 comprising the head piece, a receiver for mounting an instrument to the headpiece, and a flexible joint or connection between the head piece and the receiver.

6. The apparatus of claim 1 wherein each of the internal electrodes is fixedly attached to an internal wall defining the chamber.

7. The method of prophylaxis or treatment of tissue comprising the steps of:—
   providing a device comprising a head piece having a tissue treatment chamber with an entrance for receiving tissue and electrodes for applying electroporation to tissue;
   the electrodes comprising two internal electrodes located within the chamber on opposed sides of the chamber and two external electrodes located externally of the chamber and on opposite sides of the entrance to the chamber, the external electrodes being electrically separated so that the voltage, pulse length and/or frequency applied to the internal electrodes and the external electrodes are variable independently;
   delivering the device to a site of interest;
   drawing tissue into the chamber;
   applying a first voltage, pulse length and/or frequency to the tissue drawn into the chamber using the internal electrodes within the chamber;
   applying a second voltage, pulse length and/or frequency to the tissue external of the chamber using the external electrode;
   releasing the tissue from the chamber; and
   withdrawing the device.

8. The method of claim 7 wherein the voltage applied to the external electrodes is greater than the voltage applied to the internal electrodes.

\* \* \* \* \*